(12) United States Patent
Lee et al.

(10) Patent No.: US 8,429,986 B2
(45) Date of Patent: Apr. 30, 2013

(54) APPARATUS AND METHOD FOR GROUNDWATER SAMPLING USING HYDRAULIC COUPLERS

(75) Inventors: Bong Joo Lee, Daejeon (KR); Kyung Seok Ko, Daejeon (KR)

(73) Assignee: Korea Institute of Geoscience and Mineral Resources, Daejeon (KR)

( * ) Notice: Subject to any disclaimer, the term of this patent is extended or adjusted under 35 U.S.C. 154(b) by 293 days.

(21) Appl. No.: 12/925,167

(22) Filed: Oct. 14, 2010

(65) Prior Publication Data
US 2012/0031205 A1 Feb. 9, 2012

(30) Foreign Application Priority Data

Aug. 9, 2010 (KR) ........................ 10-2010-0076279

(51) Int. Cl.
*G01N 1/10* (2006.01)
(52) U.S. Cl.
USPC ..... 73/864; 73/863.31; 73/864.67; 73/864.66
(58) Field of Classification Search ............ 73/864, 73/864.31, 864.51
See application file for complete search history.

(56) References Cited

U.S. PATENT DOCUMENTS

| | | | |
|---|---|---|---|
| 4,857,473 A | 8/1989 | Magaritz et al. | |
| 5,327,981 A | 7/1994 | Morgan | |
| 5,725,055 A * | 3/1998 | Schirmer et al. | 166/264 |
| 6,006,613 A * | 12/1999 | Dickinson et al. | 73/864.66 |
| 6,196,074 B1 * | 3/2001 | Varhol | 73/863.23 |
| 6,276,220 B1 * | 8/2001 | Varhol | 73/863.21 |
| 6,481,300 B1 * | 11/2002 | Cordry | 73/864.65 |
| 7,178,415 B2 * | 2/2007 | Britt | 73/864.67 |
| 7,392,719 B2 * | 7/2008 | Lee et al. | 73/863.31 |

* cited by examiner

*Primary Examiner* — Hezron E Williams
*Assistant Examiner* — Mark A Shabman
(74) *Attorney, Agent, or Firm* — Rabin & Berdo, P.C.

(57) ABSTRACT

There are provided an apparatus and method for groundwater sampling, using a hydraulic coupler according to the present invention. In more particular, in the groundwater sampler which is positioned at multiple depths within a groundwater borehole to simultaneously take groundwater samples at the multiple depths, couplers are each connected to both ends of a water sampling pipe made of a metal pipe material. In case of positioning the sampler at a targeted depth, a socket and a plug forming each coupler are connected to each other, so that the both ends of the water sampling pipe—to lead groundwater to freely flow in/out. Thereafter, at the targeted depth, the sockets or plugs are permitted to be separated in the couplers at the both ends of the water sampling pipe by using a lift device, so that the both ends of the water sampling pipe are sealed to simultaneously taking groundwater samples at multiple depths.

6 Claims, 8 Drawing Sheets

APPARATUS AND METHOD FOR GROUNDWATER SAMPLING USING HYDRAULIC COUPLERS

CROSS-REFERENCE TO RELATED PATENT APPLICATION

This application claims the benefit of Korean Patent Application No. 10-2010-0076279, filed Aug. 9, 2010, in the Korean Intellectual Property Office, the disclosure of which is incorporated herein in its entirety by reference.

TECHNICAL FIELD

The present invention relates to an apparatus and method for groundwater sampling using hydraulic couplers, whereby groundwater sampling is easily and simultaneously performed in multiple depths within a borehole.

BACKGROUND

In general, groundwater sampling may be performed with a water pump or it may be performed by lowering a sampler to target depth within a single borehole. The groundwater sampling methods by pumping are divided into a volume-based purging and sampling and a low flow purging and sampling according to water pumping rate. In the former, there are indicated the problems, such as the disturbance of groundwater within a borehole according to a great amount of the groundwater being pumped, the contact of groundwater sample with air upon sampling, and the loss of volatile organic compounds. In the latter, the low flow purging and sampling method, it minimizes the disturbance of groundwater within a borehole according to the water pumping, and the amount of groundwater to be treated. However, it still has the problems, such as the change in water quality by the contact with air, and the loss of volatile organic compounds. In particular, the groundwater sampling by pumping is not suitable for profiling water quality with depth within a borehole.

Under the circumstances, it is required to develop an apparatus capable of simultaneously collecting groundwater samples for various analysis purposes at multiple depths, without having any limitations in the number of samplers to be deployed within a borehole. In addition, a sampler to be developed have to seal sample bottles under in-situ conditions, to prevent any change of the water quality by a contact with air and any loss of a volatiles, and to prevent secondary contamination during sample transfer process by making it possible for groundwater samples to be directly transferred to a laboratory, without being moved into another sample bottle.

Therefore, the present invention has been made to solve the aforementioned problems, and it is an object of the present invention to provide an apparatus and method for groundwater sampling, using hydraulic couplers, whereby the hydraulic couplers are each installed at both ends of a water sampling pipe and the sockets and plugs of couplers are separated to seal sampling pipe in-situ by air-cylinder. A number of samplers are deployed within a borehole but the groundwater samples are simultaneously taken at different targeted depths by the operation of the air-cylinders attached to each sampler.

In accordance with an aspect of the present invention, there is provided an apparatus for groundwater sampling, using hydraulic couplers, comprising: a water sampling pipe (30) with a top end connected to a second socket (21) in a single unit and a bottom end connected to a first plug (11) in a single unit; a center jacket pipe (50) receiving the water sampling pipe (30) so that the first plug (11) protrudes outside the bottom end; a first socket (12) attachably/detachably connected to the first plug (11); a second plug (22) attachably/detachably connected to the second socket (21) at an outside top end of the water sampling pipe (30); and a lift member (40) with one end connected to the second plug (22), to lift the water sampling pipe (30).

Further, the water sampling pipe (30) is connected to the second plug (22) at the top end and the first socket (12) at the bottom end, to open the both ends of the water sampling pipe (30), and thereafter, the water sampling pipe (30) is positioned at a targeted depth within a groundwater borehole, to permit a groundwater sample to flow into the water sampling pipe (30).

Further, when the water sampling pipe (30) is lifted by the lift member (40), socket covers (13) positioned at the outer circumferences of the first and second sockets (12, 21) are held by a bottom surface ($\alpha$) of the center jacket pipe (50) and by a raised part ($\beta$) formed inside the center jacket pipe (50), respectively, whereby the first socket (12) is separated from the first plug (11) and the second socket (21) is separated from the second plug (22), and the both ends of the water sampling pipe (30) are sealed.

Further, the first socket (12) is disposed in a lower jacket pipe (51) connected to the bottom end of the center jacket pipe (50), so that the first socket (12) falls into the lower jacket pipe (51) when it is separated from the first plug (11), thereby preventing the first socket (12) from being lost.

Further, a plurality of groundwater samplers are continuously connected to each other/one another lengthwise by a connection unit (W) and are positioned at multiple depths, to simultaneously take groundwater samples by depths within the borehole.

In accordance with the other aspect of the present invention, there is provided a method for groundwater sampling, using a hydraulic coupler, comprising: a step (S100) of combining a groundwater sampler by connecting a second socket (21) positioned at a top end of a water sampling pipe (30) to a second plug (22) and connecting a first plug (11) positioned at a bottom end thereof to a first socket (12), so that the both ends of the water sampling pipe (30) are open; a step (S200) of deploying a plurality of the groundwater samplers to targeted depths within a groundwater borehole; a step (S300) of sealing the both ends of the water sampling pipe (30) by lifting the water sampling pipe (30), using a lift member (40), so that the coupler sockets at the both ends of the water sampling pipe (30) are separated from the plugs, respectively; and a step (S400) of securing a groundwater sample by separating the water sampling pipe (30) from the groundwater sampler after pulling up the groundwater sampler outside the borehole.

As described above, the apparatus for groundwater sampling using the hydraulic coupler in accordance with the present invention is installed at a target depth within the groundwater borehole in the state that the water sampling pipe to retain a groundwater sample is open. Thus, it has the effect of preventing the water sampling pipe from being deformed or broken by the water pressure which increases as the depth, is deeper.

Furthermore, in accordance with the present invention, the present invention has the effect of taking samples of a great amount of groundwater by using the single water sampling pipe.

Furthermore, in accordance with the present invention, after the groundwater samplers are connected to one another and deployed, groundwater samples can be simultaneously taken at multiple depths by the single operation of the lift member.

Furthermore, in accordance with the present invention, the groundwater samples are in-situ sealed at the depth where the samples are taken. Thus, the groundwater samples can be transferred to a laboratory, without any change in water quality by contact with air and any loss of a volatile organic compound.

Furthermore, in accordance with the present invention, the water sampling pipe is re-usable after it is decontaminated. Thus, it is cost-effective and environmentally friendly.

DESCRIPTION OF DRAWINGS

These and other aspects and advantages of the present invention will become apparent and more readily appreciated from the following description of the embodiments, taken in conjunction with the accompanying drawings, in which:

FIG. 5 is a partial enlarged view illustrating Parts "A" and "B" shown in

FIG. 4;

[Brief description of reference numbers of major elements]

| | |
|---|---|
| 10: first coupler | 11: first plug |
| 12: first socket | 13: socket cover |
| 14: bottom inflow opening | 15: plug pin |
| 16: socket pin | 20: second coupler |
| 21: second socket | 22: second plug |
| 23: top inflow opening | 30: water sampling pipe |
| 40: lift member | 41: connection pipe |
| 42: groundwater inflow opening | 43: cylinder |
| 44: piston | 50: center jacket pipe |
| 50', 51', 52', 53': inflow openings | 51: lower jacket pipe |
| 52: upper jacket pipe | 53: uppermost jacket pipe |
| 60: connection ring | |
| C: connection unit | H: borehole |
| L: connection line | P: pump |
| W: wire | β: raised part |

DETAILED DESCRIPTION

It will be understood that, detailed constitution and arrangements of elements described in the detailed description or illustrated in the drawings should not be construed as limiting the application of the invention. The invention may be embodied in many alternate forms and performed in various methods.

The terms or words to describe the direction of an apparatus or element (for example, "front", "back", "up", "down", "top", "bottom", "left", "right" and "lateral", among others) are used to simplify the description of the invention. It will be, therefore, understood that these terms do not mean that the relevant apparatus or element shall be only in the specific direction. It will be further understood that, although the terms, "first", "second", etc., may be used herein to describe various elements, these elements should not be limited by these terms. These terms are only used to distinguish one element from another, not to indicate relative importance or purposes. As used herein, the singular forms "a", "an" and "the" are intended to include the plural forms as well, unless the context clearly indicates otherwise.

The present invention will now be described more fully hereinafter with reference to the accompanying drawings, in which preferred embodiments of the invention are shown. It will be understood that words or terms used in the specification and claims shall not be interpreted as the meaning defined in commonly used dictionaries. It will be further understood that the words or terms should be interpreted as having a meaning that is consistent with their meaning in the context of the relevant art and the technical idea of the invention, based on the principle that an inventor may properly define the meaning of the words or terms to best explain the invention.

Accordingly, while example embodiments of the present invention are capable of various modifications and alternative forms, embodiments of the present invention are shown by way of example in the drawings and will herein be described in detail. It should be understood, however, that there is no intent to limit example embodiments of the invention to the particular forms disclosed, but on the contrary, example embodiments of the invention are to cover all modifications, equivalents, and alternatives falling within the scope of the invention.

An apparatus and method for groundwater sampling, using hydraulic couplers according to a preferred embodiment of the present invention will be described, in detail, with reference to FIGS. 1 through 8.

As illustrated, the apparatus for groundwater sampling, using the hydraulic coupler according to the present invention comprises: a water sampling pipe 30, a first plug 11, a first socket 12, a second socket 21, a second plug 22, a lift member 40 and a lower jacket pipe 51.

The water sampling pipe 30 has a cylindrical shape with both ends being open. When a groundwater sampler 100 is positioned at a targeted depth in a groundwater borehole H in order to take a sample of groundwater, the groundwater sample flows into the water sampling pipe 30 and is stored therein.

It is obvious that the length and diameter of the water sampling pipe 30 may be variously manufactured, depending on a user's choice, to control the amount of a groundwater sample collected in the water sampling pipe 30.

Further, the water sampling pipe 30 may be painted or plated in various manners, so that the water sampling pipe 30 positioned at multiple depths within the groundwater borehole is not corroded. Or, the water sampling pipe 30 may be made of the metal or alloy material preventing its corrosion.

The second socket 21 and the first plug 11 are respectively connected to top and bottom ends of the water sampling pipe 30 in a single unit. The second socket 21 and the first plug 11 mean a coupler used when attaching to/detaching from a hydraulic hose or the like.

As disclosed in the publicly known art, the coupler comprises a plug functioning as a supply valve and a socket functioning as an inflow valve.

In brief, a plug pin 15 is formed at one end of the plug so as to be inserted and to protrude lengthwise inside the plug, and socket pin 16 is formed at one end of the socket so as to be inserted and to protrude lengthwise inside the socket.

An operation method will be described as follows: The plug is connected to the socket by backwardly pulling a socket cover 13 formed along an outer circumference of the plug. Upon the connection of the plug to the socket, as the plug pin 15 is in contact with the socket pin 16, the plug pin 15 and the socket pin 16 are each pushed in the opposite directions to each other, thereby forming a passage operatively connected between the socket and the plug. When the plug is separated from the socket, the plug pin 15 and the socket pin 16 protrude to block the passage to be closed. This is the publicly known art and therefore, further detailed description will not be presented in the detailed description of the present invention.

The center jacket pipe 50 receives the water sampling pipe 30. That is, the water sampling pipe 30 with the second socket 21 and the first plug 11 in the single unit is inserted to be installed in the center jacket pipe 50. The center jacket pipe 50 protects the water sampling pipe 30 and controls the movements of the first socket 12 connected to the first plug 11 and the second socket 21 connected to the second plug 22 when the water sampling pipe 30 moves up by the lift member 40 which will be described later. The center jacket pipe 50 will be described in detail below:

The center jacket pipe 50 comprises a plurality of inflow openings 50' locally bored lengthwise on its outer circumferential surface, to permit groundwater to flow into the center jacket pipe 50. The center jacket pipe 50 has a cylindrical shape with both ends being open.

The center jacket pipe 50 receives the water sampling pipe 30 in the manner that the first plug 11 of the water sampling pipe 30 protrudes toward the outside of a bottom end of the center jacket pipe 50.

That is, in the state that only the first plug 11 formed at the bottom end of the water sampling pipe 30 installed in the center jacket pipe 50 protrudes outside, the bottom end of the water sampling pipe 30 is supported by the inside bottom end of the center jacket pipe 50. The second socket 21 formed at the top end of the water sampling pipe 30 is supported by the inside top end of the center jacket pipe 50.

Then, a raised part ($\beta$) is formed on the inner circumferential surface of the top end of the center jacket pipe 50 so as to protrude, to prevent the second socket 21 of the water sampling pipe 30 from removing through the top end of the center jacket pipe 50. That is, a top end of the second socket 21 is held by the raised part ($\beta$) inside the center jacket pipe 50.

In the present invention, the center jacket pipe 50 is structured to have a middle end to be separable/connectable, in order to install, in the center jacket pipe 50, the water sampling pipe 30 with the second socket 21 and the first plug 11 formed at its top and bottom ends, respectively.

Namely, the water sampling pipe 30 is secured inside the center jacket pipe 50.

The lower jacket pipe 51 is connected to the bottom end of the center jacket pipe 50 so as to be extended. After the first socket 12 is connected to the first plug 11 protruding outwardly at the bottom end of the center jacket pipe 50, the lower jacket pipe 51 is connected to the center jacket pipe 50, so that the first plug 11 and the first socket 12 are positioned within the lower jacket pipe 51.

Like the center jacket pipe 50, the lower jacket pipe 51 comprises a plurality of inflow openings 51' bored on its outer circumferential surface, to permit groundwater to flow into the lower jacket pipe 51. When the first socket 12 is operatively connected to the first plug 11, the groundwater is permitted to flow into the bottom end of the water sampling pipe 30 through the other open end of the first socket 12, that is, a bottom inflow opening 14.

That is, since the first socket 12 connected to the first plug 11 is positioned at a bottom surface ($\alpha$) of the center jacket pipe 50, the groundwater cannot flow into the center jacket pipe 50.

When the water sampling pipe 30 moves up while the first plug 11 is connected to the first socket 12, the socket cover 13 positioned at the outer circumference of the first socket 12 is held by the bottom surface ($\alpha$) of the center jacket pipe 50, so that the first socket 12 is separated from the first plug 11 and thus it is positioned in the lower jacket pipe 51. Then, the lower jacket pipe 51 prevents the first socket 12 separated from the first plug 11 from being lost.

In addition, a connection ring 60 is formed at the bottom surface of the lower jacket pipe 51. When a plurality of the groundwater samplers according to the present invention is connected lengthwise, wire W or the like is used to connect the groundwater samplers to each other/one another.

The lift member 40 is positioned at the outside top end of the center jacket pipe 50. The lift member 40 forms a single unit with the second plug 22 connected to the second socket 21. That is, the lift member 40 is connected to a top end of the second plug 22 in a single unit.

When the second plug 22 moves up by the operation of the lift member 40, the whole water sampling pipe 30 connected to the second plug 22 moves up.

In more detail, the lift member 40 is connected to the other open end of the second plug 22. A connection pipe 41 is between the second plug 22 and the lift member 40, to permit the groundwater to flow into the other open end of the second plug 22, that is, a top inflow opening 23. A plurality of groundwater inflow openings 42 is bored on the outer circumferential surface of the connection pipe 41, so that the groundwater flows into the other end of the second plug 22. An upper jacket pipe 52 connected to the center jacket pipe 50 is installed outside the connection pipe 41. A plurality of inflow openings 52' is formed on the outer circumference surface of the upper jacket pipe 52. When the water sampling pipe 30 is positioned at a targeted depth within the groundwater borehole, after the groundwater within the borehole flows into the groundwater inflow openings 42 of the connection pipe 41 through the inflow openings 52' of the upper jacket pipe 52, the groundwater flowing into the groundwater inflow openings 42 is permitted to flow into the water sampling pipe 30 by passing through the second socket 21 connected to the second plug 22, through the upper inflow opening 23 of the second plug 22.

Further, an uppermost jacket pipe 53 connected to the upper jacket pipe 52 is installed outside the outer circumference of the lift member 40, to protect the lift member 40. A plurality of inflow openings 53' is formed on the outer circumferential surface of the uppermost jacket pipe 53, to permit the groundwater to flow into the uppermost jacket pipe 53. A connection ring 60 is formed on an outside top end of the uppermost jacket pipe 53, to be used when a plurality of the groundwater samplers according to the present invention needs to be continuously connected to each other/one another.

The lift member 40 may use a hydraulic lift member using a hydraulic cylinder, a pneumatic lift member using a pneumatic cylinder, an electric lift member using an electromotive cylinder or the like. The lift member may be variously applied by a user if it is for lifting the water sampling pipe 30.

The lift member 40 is connected to the ground G by a connection line (for example, hose, L). A compressor (or a nitrogen gas can, P) or the like is prepared on the ground. When pneumatic is used, air or a nitrogen gas is supplied to the inside of the lift member 40, so that a piston 44 moves up into a cylinder 43 forming the lift member 40.

Figure 8:
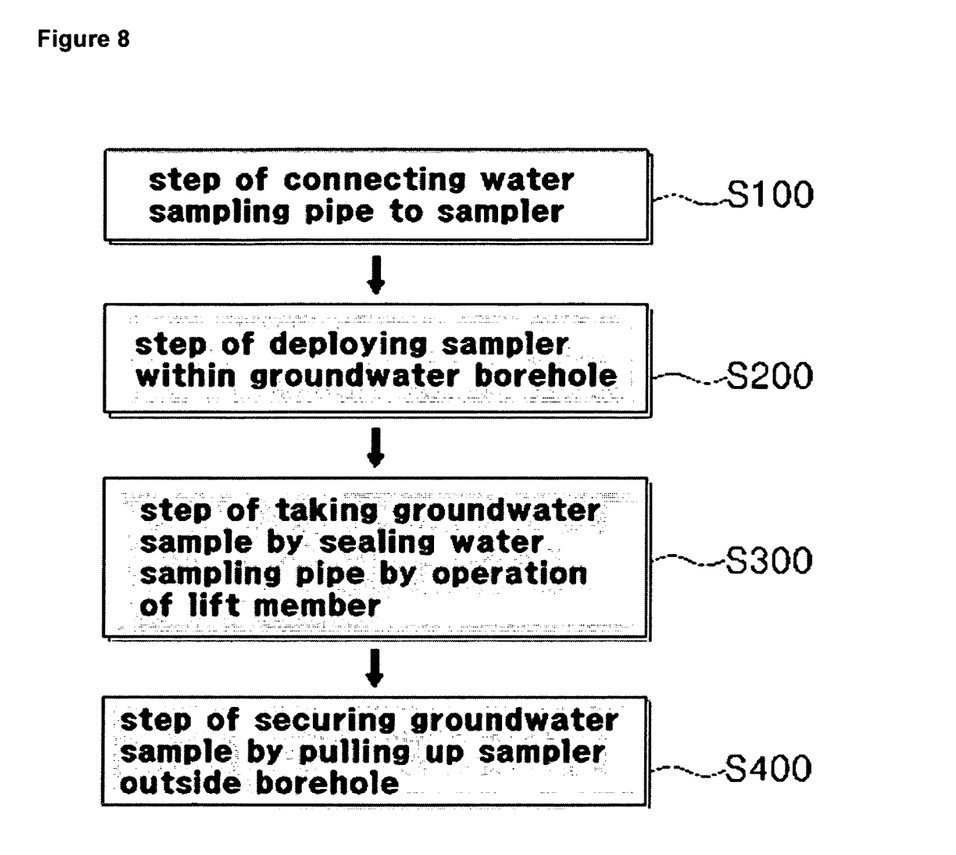
FIG. 8 is a flow chart illustrating a method of taking a sample in the groundwater sampler according to the present invention.

The operation and principle of the apparatus for groundwater sampling, using a hydraulic coupler according to the embodiment of the present invention in the above-described constitution and structure will be described below:

1. Step S100 of respectively connecting the second plug 22 and the first socket 12 to the second socket 21 and the first plug 11 positioned at the top and bottom ends of the water sampling pipe 30, so that the both ends of the water sampling pipe 30 are open: The water sampling pipe 30 with the second socket 21 and the first plug 11 connected to the top end and the bottom end in a single unit is installed in the center jacket pipe 50. The first socket 12 is connected to the first plug 11 outside the bottom end of the center jacket pipe 50, so that the first plug 11 is operatively connected to the first socket 12 and the bottom end of the water sampling pipe 30 is open. The lower jacket pipe 51 is positioned at the outside of the first plug 11 and the first socket 12 and then it is connected to the center jacket pipe 50.

The upper jacket pipe 52 is connected to the center jacket pipe 50 at the outside top end of the water sampling pipe 30 (more particularly, the center jacket pipe 50), and the second plug 22 is connected to the second socket 21, so that the second socket 21 is operatively connected to the second plug 22 and the top end of the water sampling pipe 30 is open. Then, the uppermost jacket pipe 53 is connected to the upper jacket pipe 52 outside the lift member 40.

Further, the piston 44 of the lift member 40 is maintained to protrude, at a predetermined length, outside the cylinder 43. This is to pull the piston 44 into the cylinder 43, so that the water sampling pipe 30 moves up after it is positioned at a targeted depth.

2. Step S200 of taking groundwater samples by deploying a plurality of the groundwater samplers to the targeted depth within the groundwater borehole: When a plurality of the groundwater samplers is deployed in the borehole, since the top and bottom ends of each water sampling pipe 30 are open, groundwater flows into the bottom end of the water sampling pipe 30, that is, the bottom inflow opening 14 of the first socket 12, and goes out to the top of the water sampling pipe 30, that is, the upper inflow opening 23 of the second plug 22, until the groundwater samplers arrive to the targeted depth. Therefore, the groundwater flows lengthwise while filling the inside of the water sampling pipe 30.

3. Step S300 of storing the groundwater sample in the water sampling pipe 30 by closing both ends of the water sampling pipe 30: When the piston 44 of the lift member 40 is pulled, the connection pipe 41 and the second plug 22 connected to the lift member 40 move up, thereby moving up the whole water sampling pipe 30.

The first and second sockets 12 and 21 are held respectively by the bottom surface (α) of the center jacket pipe 50 and the raised part (β) formed at the top end inside the center jacket pipe 50 and therefore these are pushed to the bottom ends so as to be separated from the first and second plugs 11 and 22, so that the both ends of the water sampling pipe 30 are sealed to take the groundwater sample.

When the lift member 40 operates, a first coupler 10 is first separated and subsequently a second coupler 20 is separated. However, since a time difference therebetween is very slight, the first coupler 10 and second coupler 20 are considered as being separated almost simultaneously. As the first and second sockets 12 and 21 are separated, the both ends of the water sampling pipe 30 are sealed, so that the groundwater sample taken at the targeted depth is kept in the water sampling pipe 30.

4. Step S400 of securing the groundwater sample by pulling up the groundwater samplers outside the borehole: When the groundwater sample is collected in the water sampling pipe 30, the sampler is pulled up on the ground and the water sampling pipe 30 separated from the groundwater sampler 100 is transferred to a laboratory.

Figure 1:
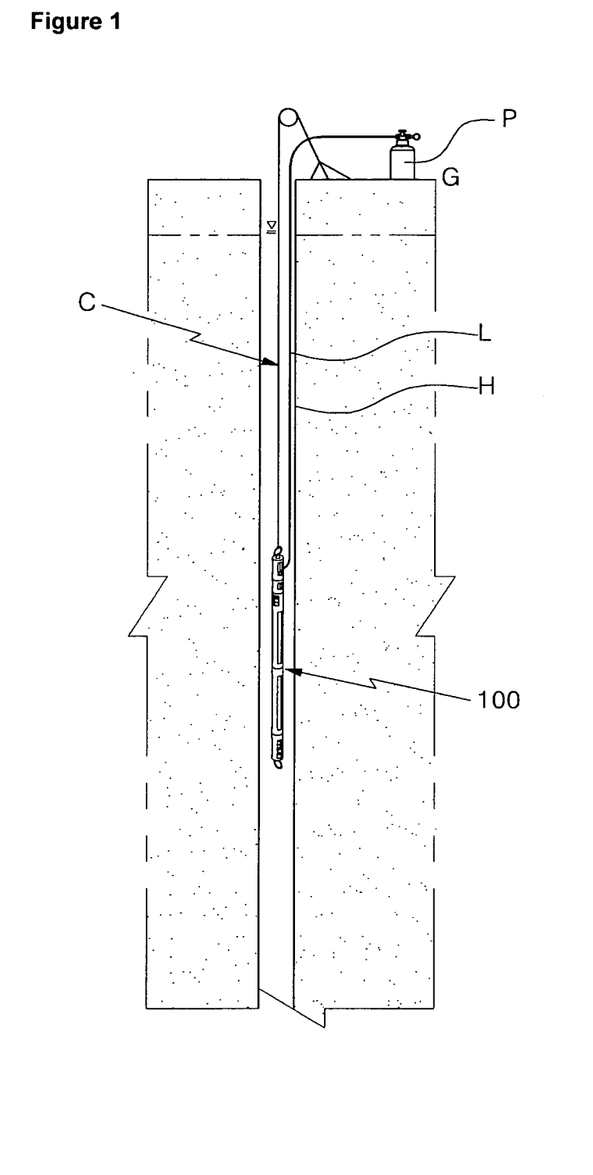
FIG. 1 is an installation view illustrating that a groundwater sampler according to the present invention is installed.
Figure 2:
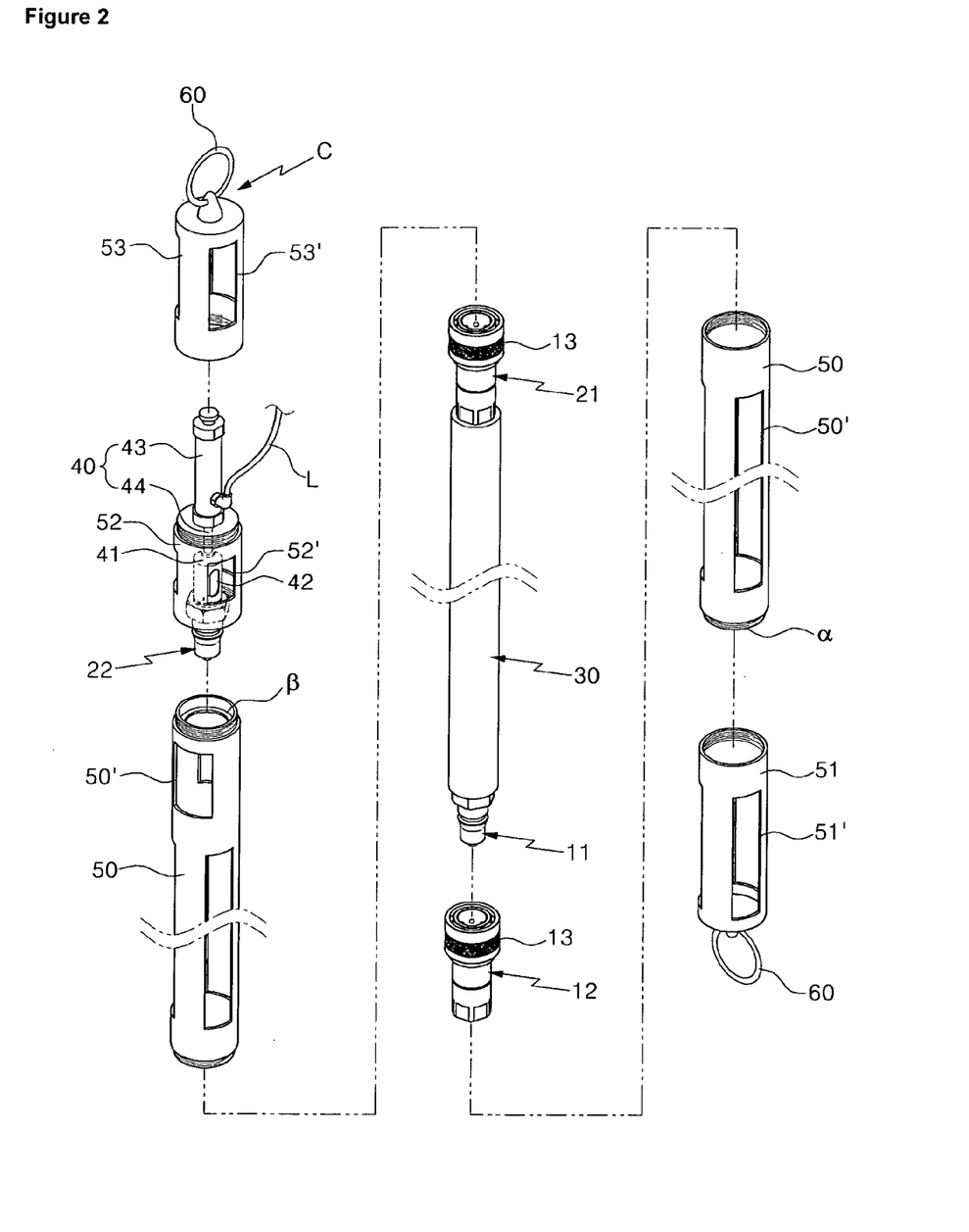
FIG. 2 is an exploded perspective view illustrating the groundwater sampler according to the present invention.
Figure 3:
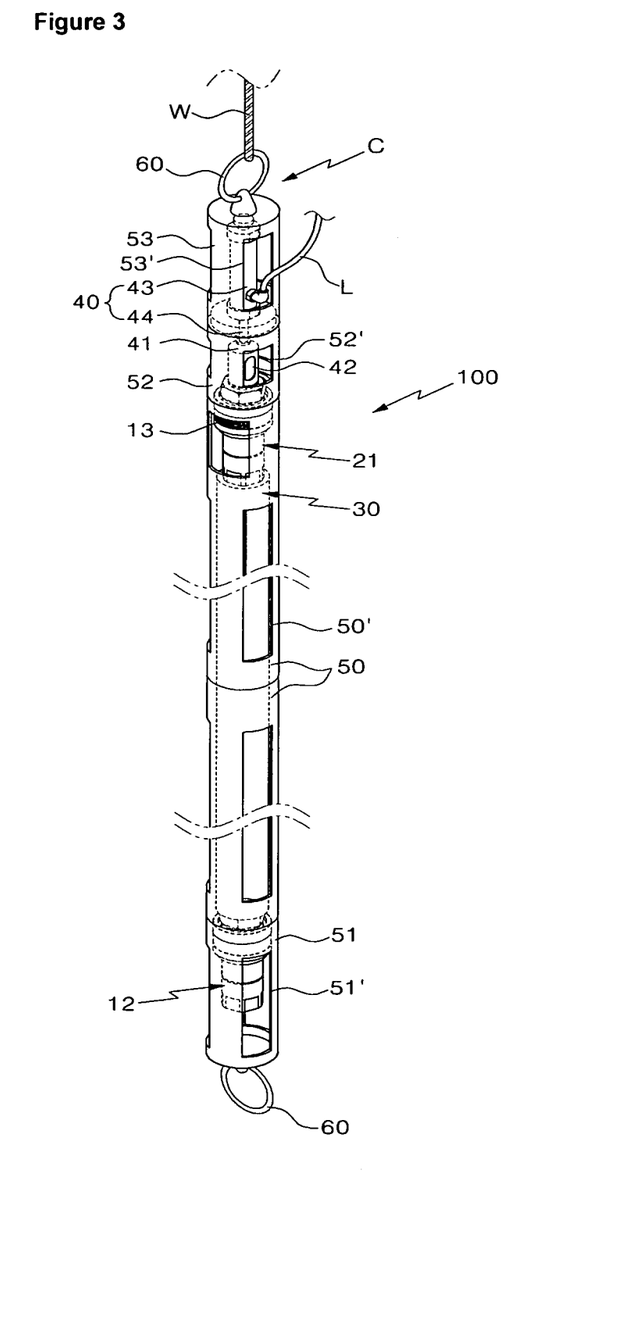
FIG. 3 is a combined perspective view illustrating the groundwater sampler of FIG. 2.
Figure 4:
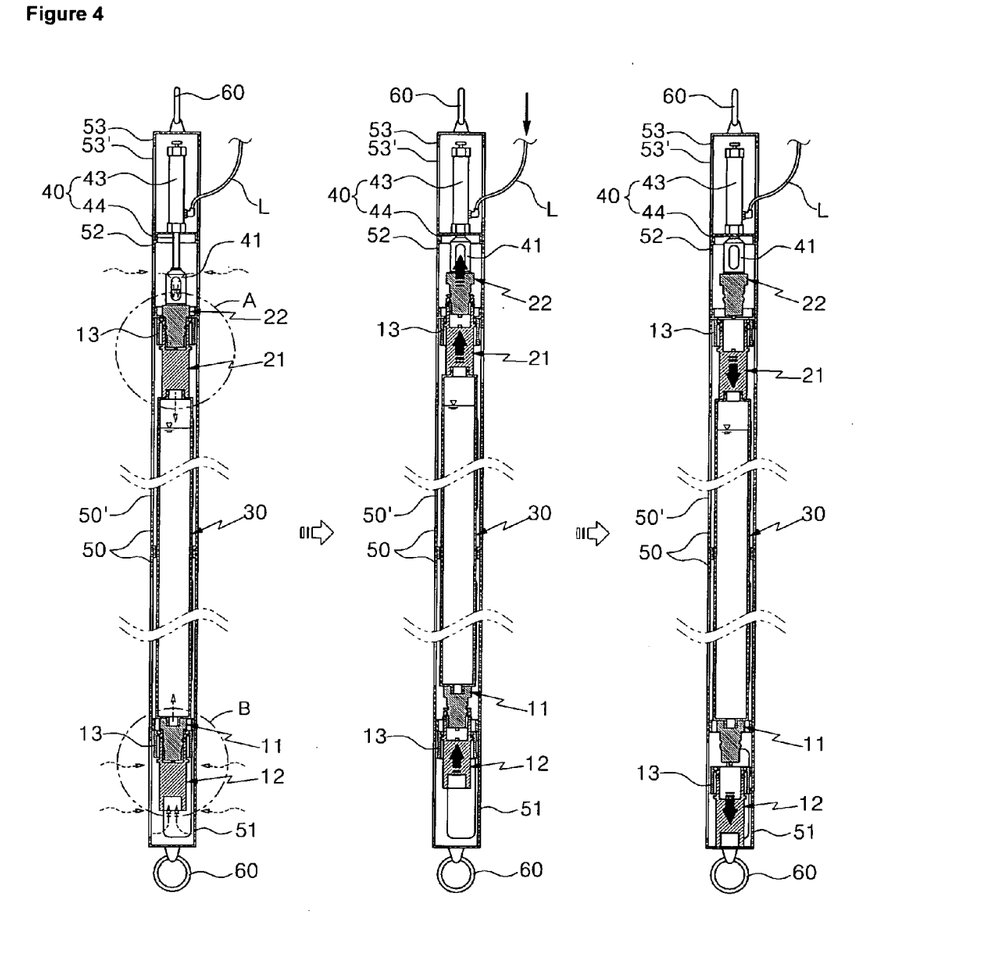
FIG. 4 is a front plan view illustrating the operation of the groundwater sampler according to the present invention.
Figure 5:
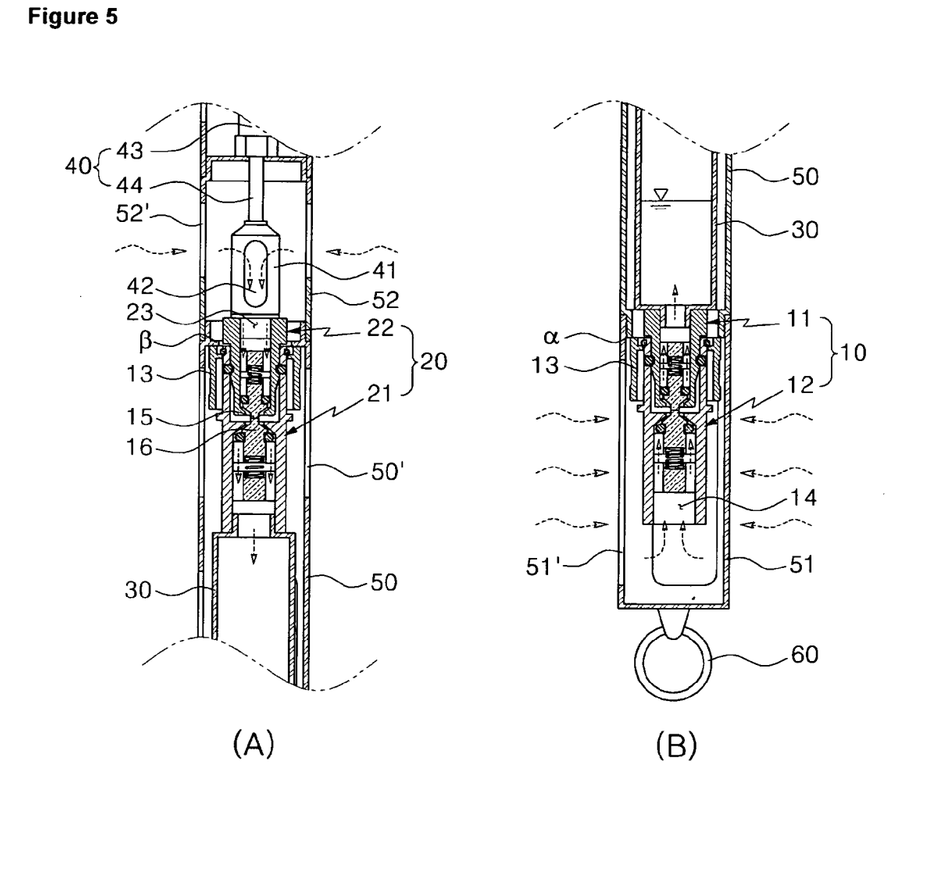
Figure 6:
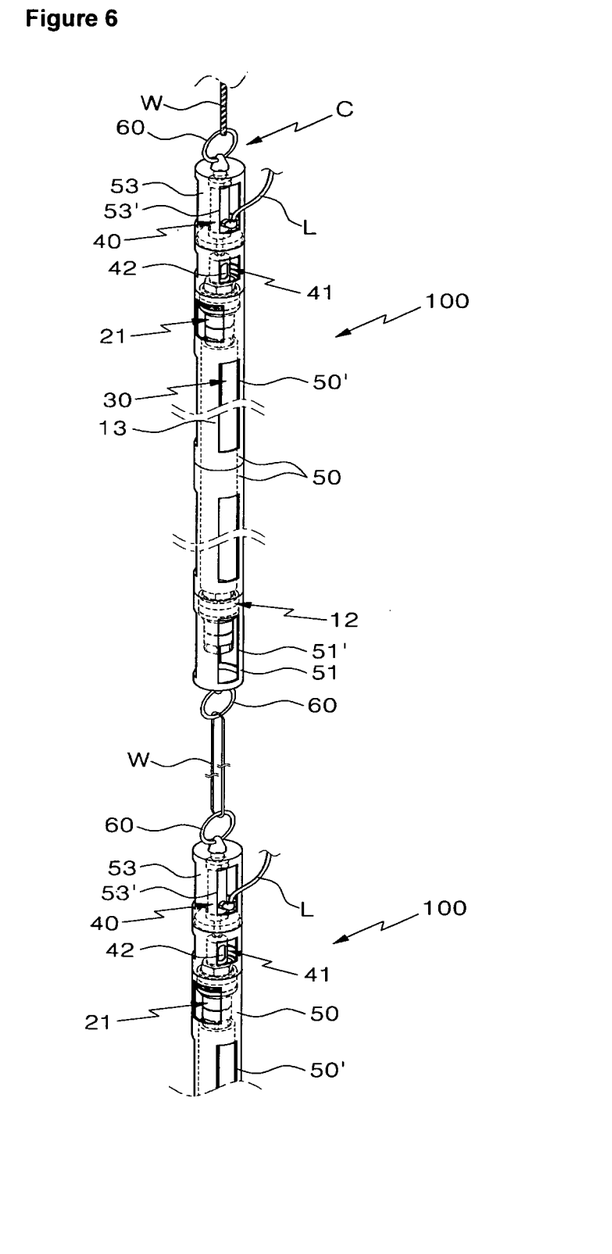
FIG. 6 is a perspective view illustrating the continuous connection of the groundwater samplers.
Figure 7:
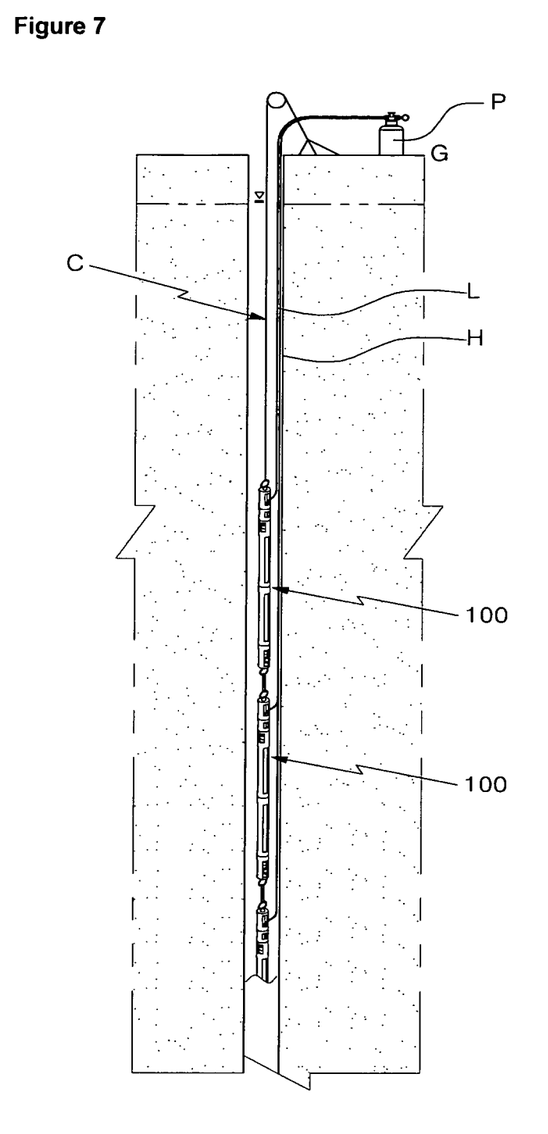
FIG. 7 is an installation view of the groundwater samplers of FIG. 6.

In accordance with the present invention, a single groundwater sampler may be used or a plurality of groundwater samplers may be used by using any one of various connection units for continuously connecting the samplers. In the present invention, the connection unit C uses the connection rings 60 formed at the top and bottom ends (the top end of the uppermost jacket pipe 53, the bottom end of the lower jacket pipe 51) of the water sampling pipe. To connect a plurality of the groundwater samplers to each other/one another, the connection rings 60 are connected by various connection lines (for example, wire, W), so that the groundwater samplers are used at the same time. Further, upon the use of a plurality of the groundwater samplers, the length of the connection wire W may be adjusted to position each water sampling pipe at a different targeted depth. (The connection ring 60 may be directly connected between the samplers.) That is, when the groundwater samplers as continuously connected to each other/one another are positioned in the groundwater borehole, each water sampling pipe is capable of taking a groundwater sample at each different depth.

Further, for the mutual connection between the jacket pipes, such as the upper jacket pipe 52 and the lower jacket pipe 51 respectively connected to the top end and the bottom end of the center jacket pipe 50, and the uppermost jacket pipe 53 connected to the upper jacket pipe 52, a female or male screw thread is formed on the outer circumference surface of the end of each pipe, the two relevant pipes are connected to each other as screwed. However, the connection structure between the pipes may vary by a user if it is capable of connecting/separating the pipes to/from each other.

Further, use of the groundwater sampler according to the present invention is not limited to groundwater. It is applicable to taking a sample of surface water, other fluids or gases.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. An apparatus for groundwater sampling, the apparatus comprising:
   a water sampling pipe having opposite upper and lower ends;
   a first plug at said lower end;
   a center jacket pipe receiving the water sampling pipe therein, the first plug protruding from a bottom end of the center jacket pipe, the center jacket pipe having a raised part inside a top end portion thereof;
   a first socket detachably attached to the first plug and including a first socket cover positioned at an outer circumference thereof;
   a second socket detachably attached to said upper end of the water sampling pipe and including a second socket cover positioned at an outer circumference thereof; and
   a lift member for lifting the water sampling pipe, the lift member including a second plug detachably attached to the second socket,
   wherein, when the water sampling pipe is lifted by the lift member, the first socket cover is held by the bottom end of the center jacket pipe and the second socket cover is held by said raised part of the center jacket pipe, so that the first socket is separated from the first plug and the second socket is separated from the second plug, thereby sealing the water sampling pipe.

2. The apparatus according to claim 1, wherein said upper and lower ends of the water sampling pipe are open when the second socket is attached to the second plug and the first plug is attached to the first socket, and thereafter, the water sampling pipe is positioned at a targeted depth within a groundwater borehole to permit a groundwater sample to flow into the water sampling pipe.

3. The apparatus according to claim 1, further comprising a connection unit to connect the apparatus to another groundwater sampling apparatus in series for simultaneously taking samples of groundwater at different depths within a groundwater borehole.

4. An apparatus for groundwater sampling, the apparatus comprising:
   a water sampling pipe having opposite upper and lower ends;
   a first plug at said lower end;
   a center jacket pipe receiving the water sampling pipe therein, the first plug protruding from a bottom end of the center jacket pipe, the center jacket pipe having a raised part inside a top end portion thereof;
   a first socket detachably attached to the first plug and including a first socket cover positioned at an outer circumference thereof;
   a second socket detachably attached to said upper end of the water sampling pipe and including a second socket cover positioned at an outer circumference thereof;
   a lift member for lifting the water sampling pipe, the lift member including a second plug detachably attached to the second socket; and
   a lower jacket pipe connected to the bottom end of the center jacket pipe,
   wherein the first socket is disposed in the lower jacket pipe so as to fall within the lower jacket pipe when it is separated from the first plug.

5. The apparatus according to claim 4, wherein said upper and lower ends of the water sampling pipe are open when the second socket is attached to the second plug and the first plug is attached to the first socket, and thereafter, the water sampling pipe is positioned at a targeted depth within a groundwater borehole to permit a groundwater sample to flow into the water sampling pipe.

6. The apparatus according to claim 4, further comprising a connection unit to connect the apparatus to another groundwater sampling apparatus in series for simultaneously taking samples of groundwater at different depths within a groundwater borehole.

* * * * *